(12) United States Patent
Ehrenreich et al.

(10) Patent No.: US 7,514,072 B1
(45) Date of Patent: Apr. 7, 2009

(54) METHOD FOR THE TREATMENT OF CEREBRAL ISCHAEMIA AND USE OF ERYTHROPOIETIN OR ERYTHROPOIETIN DERIVATIVES FOR THE TREATMENT OF CEREBRAL ISCHAEMIA

(76) Inventors: Hannelore Ehrenreich, Valentinsbreite 21, 37077 Göttingen (DE); Christoph Gleiter, Am Unteren Herrlesberg 5, 72074 Tübingen (DE)

( * ) Notice: Subject to any disclaimer, the term of this patent is extended or adjusted under 35 U.S.C. 154(b) by 260 days.

(21) Appl. No.: 09/868,089

(22) PCT Filed: Dec. 13, 1999

(86) PCT No.: PCT/EP99/09864

§ 371 (c)(1),
(2), (4) Date: Jun. 28, 2001

(87) PCT Pub. No.: WO00/35475

PCT Pub. Date: Jun. 22, 2000

(30) Foreign Application Priority Data

Dec. 14, 1998 (DE) ................................ 198 57 609

(51) Int. Cl.
*A61K 38/18* (2006.01)
*A61K 45/00* (2006.01)

(52) U.S. Cl. ............................ 424/85.1; 514/12; 514/2; 530/350; 435/69.1

(58) Field of Classification Search ................ 424/85.1; 514/12, 21, 8; 530/351; 435/69.1, 320
See application file for complete search history.

(56) References Cited

U.S. PATENT DOCUMENTS

| | | | |
|---|---|---|---|
| 4,806,524 A | | 2/1989 | Kawaguchi et al. |
| 5,013,718 A | * | 5/1991 | Adamson et al. ............... 514/8 |
| 5,614,184 A | | 3/1997 | Sytkowski et al. |
| 5,661,125 A | | 8/1997 | Strickland |
| 5,750,376 A | | 5/1998 | Weiss et al. |
| 2003/0072737 A1 | | 4/2003 | Brines et al. |

FOREIGN PATENT DOCUMENTS

| | | |
|---|---|---|
| DE | 198 57 609 A1 | 6/2000 |
| HU | P9503088 | 12/1995 |
| JP | 05-246885 | 9/1993 |
| JP | 05246885 | 9/1993 |
| WO | WO 85/02610 A1 | 6/1985 |
| WO | WO 86/03520 A1 | 6/1986 |
| WO | WO 90/11354 A1 | 10/1990 |
| WO | WO 91/06667 A1 | 5/1991 |
| WO | WO 91/09955 A1 | 7/1991 |
| WO | WO 93/09222 A1 | 5/1993 |
| WO | WO 94/12650 A2 | 6/1994 |
| WO | 94/12650 | 8/1994 |
| WO | 94/025055 | 11/1994 |
| WO | WO 95/05465 A1 | 2/1995 |
| WO | WO 95/31560 A1 | 11/1995 |
| WO | WO 96/22104 | 7/1996 |
| WO | WO 97/14307 A1 | 4/1997 |
| WO | WO 99/21966 A1 | 5/1999 |
| WO | 00/035475 | 6/2000 |
| WO | WO 00/61164 A1 | 10/2000 |

OTHER PUBLICATIONS

Bernaudin et al. A Potential Role for Erythropoietin in Focal Permanent Cerberal Ischemia in mice. Journal of Cerberal Blood Flow and Metabolism, vol. 19, No. 6, pp. 643-651. June 1999.*
Bundesverband Der Pharmazeutischen Industrie E.V., "Rote Liste 1998" entries 08 045 and 08 046, Aulendorf/Wurtt. Edition Cantor (1998).
Del Mastro et al. "Strategies for the use of Epoetin Alfa in Breast Cancer Patients" *Oncologist*, vol. 3 (5), pp. 314-318 (1998).
Marti et al. "Protective Role of Erythropoietin in Brain Ischemia" *Physiological Research*, vol. 48 (Suppl. 1) p. S14 (1999).
Ruscher et al. "Erythropoietin Protects Neurons From Oxygen/Glucose Deprivation Induced Cell Death" *Society for Neuroscience Abstracts*, vol. 24 (1-2) (1998).
Sakanaka et al. "In Vivo Evidence That Erythropoietin Protects Neurons From Ischemic Damage" *Proc. Natl. Acad. Sci. U.S.A.*, vol. 95, pp. 4635-4640, (Apr. 1998).

(Continued)

*Primary Examiner*—Bridget E Bunner
*Assistant Examiner*—Fozia M Hamud
(74) *Attorney, Agent, or Firm*—Leydig, Voit & Mayer, Ltd.

(57) ABSTRACT

The present invention relates to a method for the treatment of cerebral ischaemia and a drug for the treatment of cerebral ischaemia in particular in humans, as occurs for example in the case of stroke patients. It was found surprisingly that peripheral administering of erythropoietin to the cerebral tissue affected by the ischaemia has a distinctly protective effect. Erythropoietin has the effect thereby that the region of the cerebral tissue which is damaged permanently, in particular in the penumbra, is dramatically reduced relative to conventional measures in the case of cerebral ischaemia without erythropoietin administration.

16 Claims, 2 Drawing Sheets

OTHER PUBLICATIONS

Search Report for PCT/EP99/09864 dated Jul. 24, 2000.
Search Report for DE 198 57 609 A1 dated Jun. 15, 2000.
Albayrak et al.; "Effect of Transient Focal Ischemia on Blood-Brain Barrier Permeability in the Rat: Correlation to Cell Injury." *Acta Neuropathol*, vol. 94, 158-163 (1997).
Marti et al; "Detection of Erythropoietin in Human Liquor: Intrinsic Erythropoietin Production in the Brain," *Kidney International*, vol. 51, 416-418 (1997).
Baskaya et al., *Neuroscience Letters*, 226, 33-36 (1997).
Belayev et al., *Brain Research*, 739, 88-96 (1996).
Dietrich et al., *J. of Neuropathology and Exp. Neurlogy*, 52 (4), 351-360 (1993).
Dobbin et al., *J. of Cerebral Blood Flow and Metabolism*, 9, 71-78 (1989).
Garcia et al., *Stroke*, 27 (4), 761-765 (1996).
Kuroiwa et al., *Acta Neuropathol.* (Berl), 68, 122-129 (1985).
Masuda et al., *J. of Biological Chemistry*, 269 (30), 19488-19493 (1994).
Menzies et al., *Acta Neurochirurgica*, Suppl. 51, 220-222 (1990).
Pardridge, *J. of Cerebral Blood Flow and Metabolism*, 17 (7), 713-731 (1997).
Petito, *J. of Neuropathology and Exp. Neurology*, 38 (3), 222-234 (1979).
Saito et al., *Acta Neurochirurgica*, Suppl. 51, 186-188 (1990).
Yang et al., *Stroke*, 25 (8), 1658-1665 (1994).
U.S. Appl. No. 09/290,938, filed Apr. 13, 1989, Brines et al.
U.S. Appl. No. 09/547,220, filed Apr. 11, 2000, Brines et al.
Bradbury, M.W.B., *Circulation Research*, Aug. 1985, vol. 57, No. 2, S. 213-222.
Bundesverband Der Pharmazeutischen Industrie E.V.: "Rote Liste 1998," 1998, Aulendorf/Wurtt., Edition Cantor; DE XP002142086, NeoRecormon-Fachinfo-Service 08045.
Miyake et al., "Purification of Human Erythropoietin," *The Journal of Biological Chemistry*, vol. 252, No. 15, Issue of Aug. 10, 1977, pp. 5558-5564.
Jelkmann, "Erythropoietin: structure, control of production, and function," Physiological Reviews Apr. 1992;72(2):449-89.
Compact Wörterbuth der exakten Naturwissenschaften, 3 pages.
Expert Opinion by Marcel Leist (Apr. 30, 2007), 8 pages.
Expert Opinion by Lars Torup (Apr. 23, 2007) 7 pages.
Pschyrembel, Klinisches Wörterbuch, 2 pages.
Chekhonin et al., "Complex enzyme immunoassay testing for brain-specific proteins as a criterion for evaluation of the permeability of the hematoencephalic barriers in neuropsychic diseases," *Rossivskiv Psikhiatricheskiy Zhurnal*2:48 (1998).
Hungary Search Report.
Ay et al., *Cerebrovascular Diseases*, 9: 131-135 (1999).
Bauer et al., *Cell Mol. Neurobiol.*, 20(1): 13-28 (2000).
Boexnbaum et al., *J. Clin. Pharmacol.*, 35(10): 957-966 (1995).
Braun et al., *J. Neurochem*, 34(1): 147-152 (1980).
Bundgaard et al., *J. Histochemistry& Cytochemistry*, 3:331-336 (1981).
Cotes et al., *Bull. Wld. Hlth. Org.*, 35:751-760 (1966).
Del Mastro et al., *The Oncologist*, 3: 314-318 (1998).
Digicaylioglu et al, *Proc. Natl. Acad. Sci., USA*, 92: 3717-3720 (1995).
Ehrenreich et al., *Molecular Medicine*, 8(8): 495-505 (2002).
Ehrenreich, *Science*, 305: 183-185 (Jul. 2004).
Erbayraktar et al., *PNAS*, 100(11): 6741-6746 (May 2003).
Faris et al., *Clin. Orthop. Relat. Res.*, 357: 60-67 (1998).
Fisher et al., Current Review of Cerebrovascular Disease, 3rd Ed., 35-41, 1999.
Gaertner et al., *J. of Biological Chemistry*, 269(10): 7224-7230 (1994).
Gleiter et al., *Kidney International*, 52: 338-344 (1997).
Gleiter et al., *Clinical Pharmacology& Therapeutics*,61(6): 669-676 (1997).
Green, *Pharmacol. Ther.*, 80(2): 123-147 (1998).
Grimm et al., *Kidney International*, 38: 480-486 (1990).
Ishizuka et al., *The Journal of Pharmacology and Experimental Therapeutics*, 290(3): 1324-1330 (1999).
Jiang et al., *Journal of the Neurological Sciences*, 136: 173-179 (1996).
Krominnga et al., *Annals New York Academy of Sciences*, 257-265 (2005).
Lave et al., *J. Pharm. Pharmacol.*, 48(6): 573-577 (1996).
Lave et al., *Clin. Pharmacokinet.*, 36(3): 211-231 (1999).
Leist et al., *Science*, 305: 239-241 (Jul. 2004).
Lighthall et al., *J. Neurotrama.* 6(2): 83-97 (1989).
Lin, *Drug Metabolish and Disposition*, 26(12): 1202-1212 , 1998.
Loberg et al., *APMIS*, 101: 777-783 (1993).
Loberg et al., *APMIS*, 102(1): 771-776 (1994).
Mahmood et al., *J. Pharm. Pharmacol.*, 50(5): 493-499 (1998).
Mahmood et al., *Clin. Pharmacokinet.*, 36(1): 1-11 (1999).
Mahmood et al., *J. Pharm. Sci.*, 88(11): 1101-1106 (1999).
Marsh et al., *Kindley International*, 39: 155-163 (1991).
Masuda, et al., Anim. Cell. Technol.: Basic Appl. Aspects, Proc. Ann. Meet. Jpn. Assoc. Anim. Cell Technol., 9th(1998).
Meaney et al., J. Neurotrauma, 11(5): 599-612 (1994).
Meldrum, *American Society for Nutritional Sciences*, 1007S-1015S (2000).
Meric et al., *Brain Res.*, 638(1-2): 53-60 (1994).
Mordenti et al., Pharm. Res., 8(11): 1351-1359 (1991).
Morsihita et al., *Neurosci.*, 76(1): 105-116 (1997).
Nagao et al., *Biochemical and Biophysical Research Communications*, 188(2): 888-897 (Oct. 1992).
Nissenson, *Sem. Nephrol.*, 9 (Supppl. 2): 25-31 (1989).
Ogden, *Sem. Nephrol.*, 9 (Suppl. 2): 12-15 (1989).
Pantoliano et al., *Biochemistry*, 26: 2077-2082 (1987).
Plotkin et al., *Brain Res.*, 881(1): 57-61 (2000).
Rifkind et al., *Life Sci.*, 64(4): 237-247 (1999).
Rowland et al., Principles of Neural Science, 3rd Edition, 1050-1060 , 1991.
Sadamoto et al, *Biochem. and Biophys. Research Communications*, 253: 26-32 (1998).
Siren et al., *PNAS*, 98(7): 4044-4049 (2001).
Stenesh, Dictionary of Biochemistry and Molecular Biology, 2nd Edition, John Wiley & Sons , 1989.
Suzuki et al., *Acta Neuropathol.* (Berl.), 60: 207-216 (1983).
Sweeney et al., *Can. J. Physiol. Pharmacol.*, 73: 1525-1535 (1995).
Zhang et al., *Journal of Neuroscience Research*, 83: 1241-1251 (2006).
Tatlisumak et al., "Effect of Basic Fibroblast Growth Factor on Experimental Focal Ischemia Studied by Diffusion-Weighted and Perfusion Imaging," *Stroke*, 27: 2292-2298.
Dyker et al., "Duration of Neuroprotective Treatment for Ischemic Stroke," *Stroke*, 29: 535-542 (1998).
"Recommendations for Standards Regarding Preclinical Neuroprotective and Restorative Drug Development," *Stroke*, 30: 2752-2758 (1999), Syair.
Bernaudin et al., "A Potential Role for Erythropoietin in Focal Permanent Cerebral Ischemia in Mice," *Journal of Cerebral Blood Flow and Metabolism*, 19: 643-651 (1999).
Brines et al., "Erythropoietin Crosses the Blood-Brain Barrier to Protect Against Experimental Brain Injury," *Proceedings of the National Academy of Sciences*, 97 (19): 10526-10531 (2000).
Hunter et al., "Animal Models of Acute Ischaemic Stroke: Can They Predict Clinically Successful Neuroprotective Drugs?, " *TiPS*, 16: 123-128 (1995).
Hossmann, "Experimental Models for the Investigation of Brain Ischemia," *Cardiovascular Research*, 39:106-120 (1998).
Sasaki et al., "Erythropoietin: Multiple Physiological Functions and Regualtion of Biosynthesis," *Biosci. Biotechnol. Biochem.*, 64(9): 1775-1793 (2000).
Tagami et al., "Insulin-Like Growth Factor-1 Attenuates Apoptosis in Hippocampal Neurons Caused by Cerebral Ischemia and Reperfusion in Stroke-Prone Spontaneously Hypertensive Rats," *Laboratory Imagination*, 76(5): 613-617 (1997).
Hunt Bobo et al., "Convection-enhanced Delivery of Macromolecules in the Brain," *Proc. Natl. Acad. Sci. USA*, 91: 2076-2080 (1994).
Guan et al., "The Movement of IGF-1 Into the Brain Parenchyma After Hypoxic-Ischaemic Injury," *Neuroreport*, 7:632-636 (1996).

Rordorf et al., "Regional Ischemia and Ischemic Injury in Patients With Acute Middle Cerebral Artery Stroke as Defined by Early Diffusion-Weighted and Perfusion-Weighted MRI," *Stroke*, 29(5); 939-943 (1998).

Hsu, C.Y., "Editorial Comment," *Stroke*, 27(12): 2298, (Dec. 1996).

Fisher et al., "Delayed Treatment with Intravenous Basic Fibroblast Growth Factor Reduces Infarct Size Following Permanent Focal Cerebral Ischemia in Rats," *Journal of Cerebral Blood Flow and Metabolism*, 15(6):953-959 (1995).

Masuda et al., "Functional Erythropoietin Receptor of the Cells with Neural Characteristics," *Journal of Biological Chemistry*, 268(15): 11208-11216 (1993).

Dietrich et al., "Moderate Hyperglycemia Worsens Acute Blood-Brain Barrier Injury After Forebrain Ischemia in Rats," *Stroke*, 24(1): 111-116 (1993).

Maness et al., "Selective Transport of Blood-Borne Interleukin-1α Into the Posterior Division of the Septum of the Mouse Brain," *Brain Research*, 700:83-88 (1995).

Banks et al., "Peptide Transport Systems for Opiates Across the Blood-Brain Barrier," *American Journal of Physiology*, 259(1): E1-E10 (1990).

Pan et al., "Permeability of the Blood-Brain and Blood-Spinal Cord Barriers to Interferons," *Journal of Neuroimmunology*, 76: 105-111 (1997).

Banks et al., "Penetration of Interleukin-6 Across the Murine Blood-Brain Barrier," *Neuroscience Letters*, 179: 53-56 (1994).

Banks et al., "Passage of Pituitary Adenylate Cyclase Activating Polypeptide $_{1-27}$ and Pituitary Adenylate Cyclas Activating Polypeptide $_{1-38}$ Across the Blood-Brain Barrier," *Journal of Pharmacology and Experimental Therapeutics*, 267(2): 690-696 (1993).

Waguespack et al., "Interleukin-2 Does Not Cross the Blood-Brain Barrier by a Saturable Transport System," *Brain Research Bulletin*, 34(2): 103-109 (1994).

Banks et al., "HIV-1 Protein GP120 Crosses the Blood-Brain Barrier: Role of Adsorptive Endocytosis," *Life Sciences*, 61(9): 119-125 (1997).

Banks et al., "Transport of Insulin Across the Blood-Brain Barrier: Saturability at Euglycemic Doses of Insulin," *Peptides*, 18(9): 1423-1429 (1997).

Banks et al., "Regional Variation in Transport of Pancreatic Polypeptide Across the Blood-Brain Barrier of Mice," *Pharmacology Biochemistry and Behavior*, 51(1): 139-147 (1995).

Maness et al., "Passage of Human Amyloid β-Protein 1-40 Across the Murine Blood-Brain Barrier," *Life Sciences*, 55(21): 1643-1650 (1994).

Banks et al., "Leptin Enters the Brain by a Saturable System Independent of Insulin," *Peptides*, 17(2): 305-311 (1996).

English Translation of Summons to Oral Proceedings Before European Patent Office Board of Appeal, and Annex to Summons, dated Feb. 7, 2008, 11 pages, rapporteur.

English Translation of Second Statement of Dr. Max Gassmann, submitted to the EPO in connection with opposition proceedings of EP 99966958.3, (Sep. 8, 2007).

English Translation of Statement of Dr. Anna-Leena Kaarina-Siren, submitted to the EPO in connection with opposition proceedings of EP 99966958.3, (Nov. 14, 2007).

English Translation of Statement of Dr. Wolfgang Jelkmann, submitted to the EPO in connection with opposition proceedings of EP 99966958.3, (Nov. 22, 2007).

Statement of Dr. Ryuzo Sasaki, submitted to the EPO in connection with opposition proceedings of EP 99966958.3, (Sep. 16, 2007).

Declaration of Dr. Friedrich Lottspeich, with Annex I (Aug. 14, 2007).

Final Decision of the Opposition Division, dated Sep. 10, 2008.

"Shire In-License Novel Tissue Protective Cytokine Technology From Warren Pharmaceuticals," Press Release Oct. 3, 2006, Warren Pharmaceuticals, Ossining, New York, USA.

"Response to Communication pursuant to Art. 96(2) EPC dated Mar. 19, 2004" filed Sep. 29, 2004, Kenneth S. Warren Institute, Inc., EP Application No. 00923344.6.

* cited by examiner

METHOD FOR THE TREATMENT OF CEREBRAL ISCHAEMIA AND USE OF ERYTHROPOIETIN OR ERYTHROPOIETIN DERIVATIVES FOR THE TREATMENT OF CEREBRAL ISCHAEMIA

CROSS REFERENCE TO RELATED PATENT APPLICATIONS

This patent application claims the benefit of PCT Application No. PCT/EP99/09864, filed on Dec. 13, 1999, which claims priority to German patent application 198 57 609.9 filed on Dec. 14, 1998.

FIELD OF THE INVENTION

The present invention relates to a method for the treatment of cerebral ischaemia and a drug for the treatment of cerebral ischaemia in mammals, in particular in humans, such as occur for example in the case of stroke patients.

BACKGROUND OF THE INVENTION

In the case of an ischaemic brain infarction, the damaged regions are divided into the ischaemic core zone and the so-called penumbra which surrounds the core. The size of the ischaemic core plus penumbra determines the extent of the damage after ischaemic insult.

Erythropoietin, also called "EPO" for short, is a glycoprotein which occurs naturally in the body with a molecular weight of 30,000 Dalton (W. Jelkman, "Erythropoietin: Structure, Control of Production, and Function", Physiological Reviews, 1992, Volume 72, Pages 449 to 489). It is an essential growth factor for the production of erythrocytes and was isolated for the first time in 1977.

Erythropoietin has been in frequent clinical use for many years in the case of patients with renal anaemia on kidney dialysis, in order to obtain larger quantities of autologue blood before planned operations and it also hit the newspaper headlines as a blood-doping agent.

Erythropoietin proved itself thereby to be exceedingly well tolerated. The side effects which are relevant are in particular the often therapeutically desired stimulation of the haematopoiesis with polyglobulia and an arterial hypertension which is seldom to be seen. Both effects are to be expected mainly after chronic erythropoietin administering. If necessary, they are relatively easy to remedy by medicinal treatment or by blood-letting.

Intolerance reactions or anaphylactic reactions constitute rarities in the case of erythropoietin.

To date there is no effective therapy for cerebral ischaemia, such as for example for the treatment of stroke patients without operating on the head region of the patient.

In PNAS 1998, Volume 95, No. 8, pages 4635 to 4640, Sakanaka et al. disclose that central administration of erythropoietin in animal experiments offers a protective effect on cerebral neurons. Because of the knowledge that the blood brain barrier cannot be surmounted by larger proteins, erythropoietin is administered directly to the brain tissue, i.e. by direct infusion, in experiments; however such direct infusion is ruled out in humans because of the high risks which are associated with the application and the maintenance of a temporary ventricle drainage, for example of infections or bleeding.

DelMastro L. et al. disclose in Oncologist 1998, 3/5, pages 314-318 that the preventive administering of erythropoietin can prevent anaemia in cancer patients who have been treated with chemotherapy and hence can preventively reduce the risk of such patients with respect to cerebral ischaemia as a result of anaemia caused by chemotherapy. A therapy for an already present cerebral ischaemia, in particular in the case of patients not treated with chemotherapy, is not disclosed therein.

It is thus the object of the present invention to make available a method for the treatment of cerebral ischaemia, a drug for usage in the treatment of cerebral ischaemia and also a means for producing a drug for the treatment of cerebral ischaemia, which can be applied simply and with as few side effects as possible and which is also risk-free.

BRIEF SUMMARY OF THE INVENTION

The invention is directed to a method for the treatment of cerebral ischaemia in mammals comprising administering erythropoietin to a mammal. The erythropoietin is administered peripherally to the mammal. In one embodiment, the erythropoietin is administered intravenously to the mammal.

BRIEF DESCRIPTION OF THE DRAWINGS

FIG. 1A illustrates the average of the serum concentration of four stroke patients that were intravenously administered a dose of 35,000 IU human recombinant erythropoietin at approximately 8 h, 24 h, and 48 h after the stroke. FIG. 1B illustrates the concentrations of EPO in (a) six control patients with nonischemic neurological illnesses after infusion of erythropoietin, (b) two untreated stroke patients without infusion of erythropoietin, and (c) four stroke patients after infusion of erythropoietin.

FIG. 2A illustrates three section views from underneath during the course of the therapy through the brain of the patient approximately 7 hours after the stroke. FIG. 2B illustrates the damaged regions that can be detected approximately 3 days after the stroke. FIG. 2C illustrates the same section views after 18 days.

DETAILED DESCRIPTION OF THE INVENTION

Figure 1:
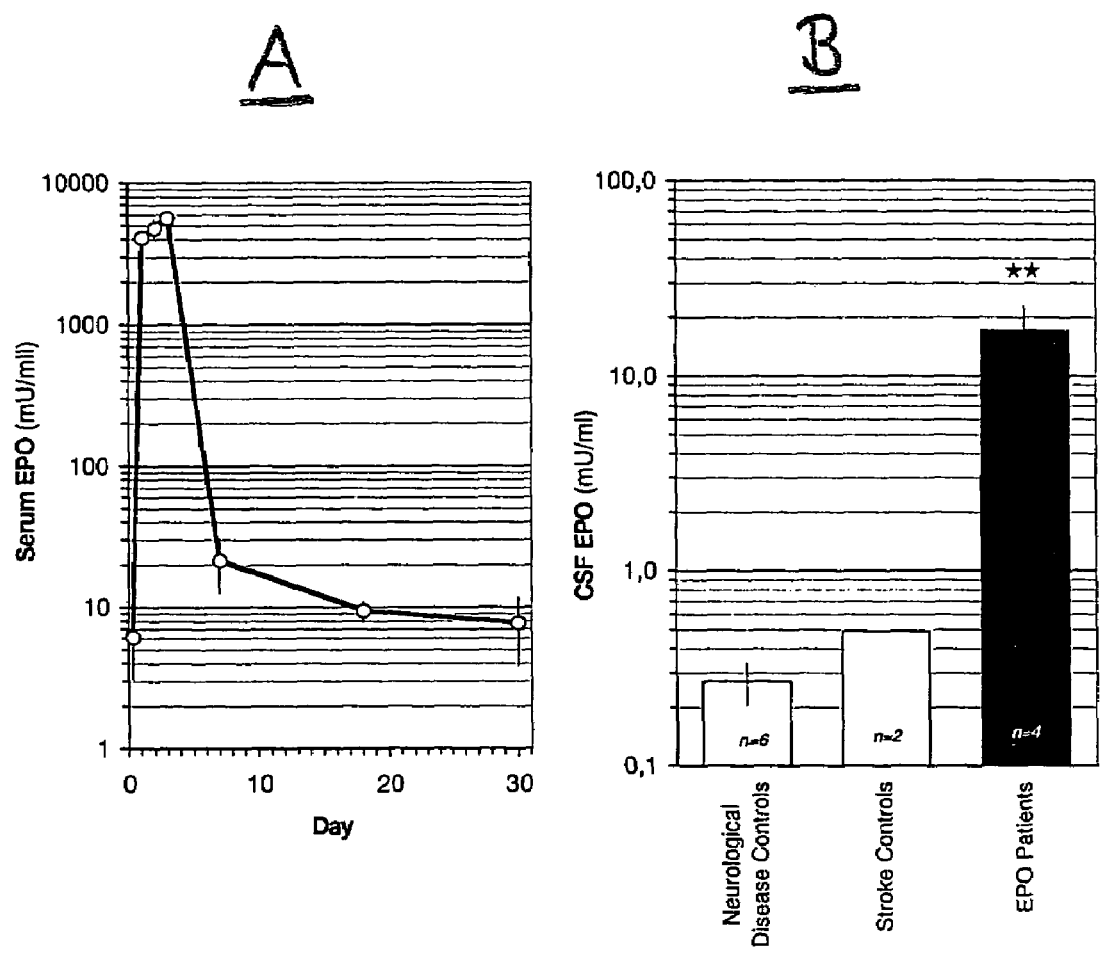
FIG. 1 illustrates the occurrence of erythropoietin in serum and in the cerebrospinal fluid after a stroke. More specifically.

The starting point of the method according to the invention and the usages of erythropoietin according to the invention is that, after an ischaemia has taken place, for example after a stroke, as much as possible of the damaged brain tissue, in particular the penumbra, should be saved as soon as possible. It was found that peripheral administering of erythropoietin has a distinctly protective effect on the cerebral tissue affected by the ischaemia. Erythropoietin has the effect thereby that the region of the damaged cerebral tissue, in particular in the penumbra, is dramatically reduced relative to conventional measures in the case of cerebral ischaemia without erythropoietin administration.

This unexpected tissue-saving effect of peripherally administered erythropoietin in cerebral ischaemia in humans should not be taken for granted since erythropoietin is usually not able to surmount the blood brain barrier as it is known as a larger protein with a molecular weight of approximately 30,000 Dalton. A directly intraventricular administering of erythropoietin, i.e. direct infusion of erythropoietin into the brain tissue, is however ruled out in humans usually because of the risks which are associated with the application and the maintenance of a temporary ventricular drainage, such as of infections or bleeding.

It is the contribution of the present invention to detect and make it feasible that, surprisingly for the treatment of a cerebral ischaemia which has occurred, erythropoietin can be given peripherally as a drug directly after the damaging occurrence and then it passes into the damaged brain area and becomes effective.

Peripheral administering of erythropoietin, i.e. on this side of the blood brain barrier, is effected advantageously intramuscularly or vascularly. A directly vascular administering, which as is known advantageously with drugs should generally be effected intravenously, is presented here directly in order to bring erythropoietin in contact with the damaged cerebral tissue in one high dose within a short period of time i.e. as quickly as possible after the damaging occurrence.

It can thus be assumed therefrom that erythropoietin can surmount the blood brain barrier in the damaged regions directly after damage to the brain tissue by ischaemia. It is therefore possible to administer a drug which contains erythropoietin to the patient who has for example been damaged by a stroke, the erythropoietin actually reaching the damaged brain tissue.

Hence for the first lime an effective therapeutic agent is available for cerebral ischaemia in mammals, particularly in humans such as for example in the case of a stroke.

It is furthermore advantageous thereby that the intact blood brain barrier in the non-damaged cerebral tissue regions effectively prevents furthermore penetration of the erythropoietin which is not required there and therefore the tissue regions which are not affected by the ischaemic infarction are not affected by the therapy, i.e. no side effects or only greatly reduced side effects can occur.

Erythropoietin is applied as a drug advantageously with a dosage at an amount of 5,000 to 100,000 units, ideally 35,000 units, per dose, possibly with a daily dose in the first days, for the first time possibly within 8 hours after the stroke. Merely a few doses of erythropoietin suffice thereby to produce the therapeutic effect. Furthermore this has the advantage that the side effects and risks, which are mainly observed in lengthy continuous treatments of other syndromes according to the above-described state of the art, cannot occur or only slightly when using erythropoietin for treating cerebral ischaemia.

Erythropoietin is known from prior art. Human erythropoietin was first isolated from urine (T. Miyake et al 1977, J. Biol. Chem., Volume 252, pages 5558-5564). Today production is effected by DNA recombination. Using this method it can be produced in adequate quantities and be used according to the invention. Further variants of erythropoietin with an altered amino acid sequence or structure or also fragments with the functional sequences portions which are relevant for the biological function of erythropoietin can be used for the usage according to the invention and should be included in the term "erythropoietin" as is used in this application. Variability of the erythropoietin variants which can be used according to the invention is produced furthermore from modifications in glycosilation of erythropoietin.

Consequently the erythropoietin to be used according to the invention can concern inter alia human erythropoietin, as it occurs naturally, or else erythropoietin products or erythropoietin analogues (in general: erythropoietin variants or derivatives), which have modifications of natural human erythropoietin, such as for example modifications to the sequence such as deletions and substitutions, or else modifications to the carbohydrate compositions. Such erythropoietin products can be produced by different production methods. Such production methods for erythropoietin variants, derivatives or analogues which can be used according to the invention are for example described in the patent applications WO 86/03520, WO 85/02610, WO 90/11354, WO 91/06667, WO 91/09955, WO 93/09222, WO 94/12650, WO 95/31560 and WO 95/05465, the disclosures of which should all hereby be contained in their entirety in the disclosure content in the present patent application by reference hereto and should be included in the present patient application.

In the following, examples of the method according to the invention and the usages according to the invention are given.

EXAMPLES

In FIG. 1A, the average of the serum concentration of four patients with strokes, i.e. whose peripheral concentration of erythropoietin is measured over several days to whom at approximately 8 hours, approximately 24 hours and again approximately 48 hours after the stroke were given respectively a dose of 35,000 IE human recombinant erythropoietin (preparation "Neorecormon" by the Hoffmann LaRoche AG company) intravenously. It can be detected that the serum concentration achieves its maximum within the first few days and then decreases sharply subsequently.

In FIG. 1B, the concentrations of EPO are represented in six control patients with non-ischaemic neurological illnesses ("neurological disease controls") after infusion of erythropoietin, in two untreated stroke patients ("stroke controls") without infusion of erythropoietin and also in four stroke patients ("EPO patients") after infusion of erythropoietin as in the case of the control patients. There is represented thereby the average of the EPO concentration in the cerebrospinal fluid, as was determined on average 6.4 hours after a first infusion of 35,000 IE human recombinant erythropoietin (preparation "Neorecormon" by the Hoffmann LaRoche AG company). The four stroke patients ("EPO patients") concern the same patients as in FIG. 1A.

Taking into account the logarithmic scale used in the illustration in FIG. 1B it can be directly detected that the concentration of erythropoietin in the cerebrospinal fluid in stroke patients ("EPO patients") is approximately 100 times above that of control patients treated in the same manner ("neurological disease controls") or also the untreated stroke patients ("stroke controls").

It is the contribution of the present invention to recognise that in the case of a cerebral ischaemia the blood brain barrier is permeable for erythropoietin so that in order to treat a cerebral ischaemia directly after the damaging occurrence erythropoietin can pass peripherally as a drug into the damaged brain area and can become effective.

Figure 2:
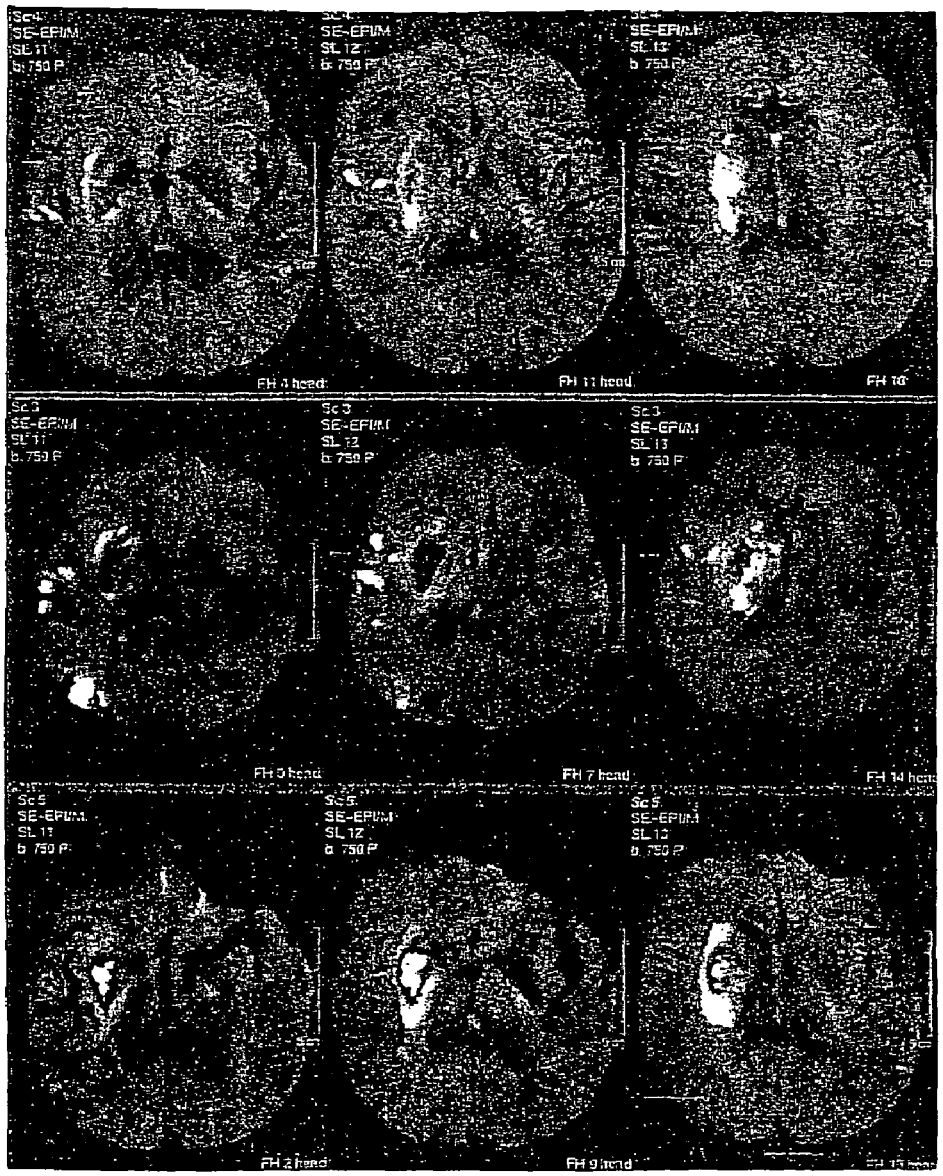
FIG. 2 illustrates the size of the lesion after cerebral ischemia. In particular.

FIG. 2 shows the extent of the lesion after a stroke in the case of a 73 year-old patient. The illustrated pictures were produced by means of magnetic nuclear resonance spectroscopy ("diffusion weighted MRI").

The patient was infused intravenously approximately 8 hours after a stroke with 35,000 IE human recombinant erythropoietin (preparation "Neorecommon" of the Hoffmann LaRoche AG company). Approximately 24 hours and 48 hours after the stroke a further equally large dose of erythropoietin respectively was given.

FIG. 2A shows thereby three section views from underneath during the course of the therapy through the brain of the patient approximately 7 hours after the stroke. The regions damaged by the stroke can be clearly seen offset by their white colouration.

In FIG. 2B, the damaged regions can be detected approximately 3 days after the stroke likewise by their whitish colouration (with a dark centre).

FIG. 2C shows the same section views after 18 days. It can be clearly seen that the result was a marked reduction in the primary lesion. This reduction in the ischaemic infarction area can be ascribed inter alia to treatment with erythropoietin.

The invention claimed is:

1. A method for the treatment of cerebral ischaemia in mammals, comprising administering erythropoietin to a mammal affected by cerebral ischaemia, wherein the erythropoietin is administered peripherally in an amount of 5,000 IU to 100,000 IU per dose to the mammal.

2. The method according to claim 1, wherein the erythropoietin is administered vascularly.

3. The method according to claim 1, wherein the erythropoietin is administered intravenously.

4. The method according to claim 1, wherein the erythropoietin is administered for the treatment of strokes.

5. The method according to claim 1, wherein the erythropoietin is administered in an amount of 35,000 IU per dose.

6. The method according to claim 1, wherein the erythropoietin is native, recombinant, human, or animal erythropoietin, or a derivative thereof.

7. The method according to claim 1, wherein the mammal is a human.

8. A method for the treatment of cerebral ischaemia in mammals, comprising administering erythropoietin intravenously to a mammal affected by cerebral ischaemia, wherein the erythropoietin is administered in an amount of 5,000 IU to 100,000 IU per dose.

9. A method for the treatment of cerebral ischaemia in mammals, comprising administering erythropoietin to a mammal affected by cerebral ischaemia, wherein the erythropoietin is administered peripherally in an amount of 5,000 IU to 100,000 IU per day to the mammal.

10. The method according to claim 9, wherein the erythropoietin is administered vascularly.

11. The method according to claim 9, wherein the erythropoietin is administered intravenously.

12. The method according to claim 9, wherein the erythropoietin is administered for the treatment of strokes.

13. The method according to claim 9, wherein the erythropoietin is administered in an amount of 35,000 IU per day.

14. The method according to claim 9, wherein the erythropoietin is native, recombinant, human, or animal erythropoietin, or a derivative thereof.

15. The method according to claim 9, wherein the mammal is a human.

16. A method for the treatment of cerebral ischaemia in mammals, comprising administering erythropoietin intravenously to a mammal affected by cerebral ischaemia, wherein the erythropoietin is administered in an amount of 5,000 IU to 100,000 IU per day.

* * * * *